United States Patent
McLaughlin et al.

(10) Patent No.: US 6,906,202 B2
(45) Date of Patent: Jun. 14, 2005

(54) PURIFIED RACEMIC LASOFOXIFENE AND PURIFIED LASOFOXIFENE D-TARTRATE AND A METHOD FOR EFFECTIVE PURIFICATION OF RACEMIC LASOFOXIFENE

(75) Inventors: Robert W. McLaughlin, Groton, CT (US); Harry A. Watson, Jr., Groton, CT (US); Constantine Sklavounos, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/397,654

(22) Filed: Mar. 26, 2003

(65) Prior Publication Data

US 2003/0212122 A1 Nov. 13, 2003

Related U.S. Application Data

(60) Provisional application No. 60/368,872, filed on Mar. 28, 2002.

(51) Int. Cl.$^7$ ............................................. C07D 207/04
(52) U.S. Cl. ...................................................... 548/570
(58) Field of Search ........................................... 548/570

(56) References Cited

U.S. PATENT DOCUMENTS

| | | | | |
|---|---|---|---|---|
| 5,552,412 | A | 9/1996 | Cameron et al. | 514/317 |
| 5,948,809 | A | 9/1999 | Chiu et al. | 514/428 |
| 6,153,622 | A | 11/2000 | Cameron et al. | 514/307 |
| 6,180,375 | B1 | 1/2001 | Truesdell | 435/121 |
| 6,204,286 | B1 | 3/2001 | Cameron et al. | 514/428 |
| 6,232,476 | B1 | 5/2001 | Chiu | 549/430 |
| 6,441,193 | B1 | 8/2002 | Cameron et al. | 548/528 |

*Primary Examiner*—Golam M M Shameem
(74) *Attorney, Agent, or Firm*—Peter C. Richardson; Gregg C. Benson; John A. Wichtowski

(57) ABSTRACT

A method for removing impurities from racemic cis-6-phenyl-5-[4-(2-pyrrolidin-1-ylethoxy)phenyl]-5,6,7,8-tetrahydronaphthalen-2-ol and purified cis-6-phenyl-5-[4-(2-pyrrolidin-1-ylethoxy)phenyl]-5,6,7,8-tetrahydronaphthalen-2-ol useful as an estrogen agonist/antagonist.

11 Claims, No Drawings

PURIFIED RACEMIC LASOFOXIFENE AND PURIFIED LASOFOXIFENE D-TARTRATE AND A METHOD FOR EFFECTIVE PURIFICATION OF RACEMIC LASOFOXIFENE

CROSS REFERENCE TO RELATED APPLICATION

This application claims priority from U.S. provisional application No. 60/368,872 filed Mar. 28, 2002.

BACKGROUND OF THE INVENTION

The present invention relates to a process for removing impurities from a racemic mixture of cis isomers of a compound of Formula I, cis-6-phenyl-5-[4-(2-pyrrolidin-1-ylethoxy)phenyl]-5,6,7,8-tetrahydronaphthalen-2-ol, (hereinafter "racemic lasofoxifene" or "racemate").

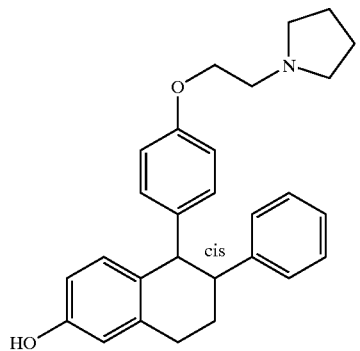

This invention also relates to a purified racemic lasofoxifene, cis-6-phenyl-5-[4-(2-pyrrolidin-1-ylethoxy)phenyl]-5,6,7,8-tetrahydronaphthalen-2-ol, (hereinafter "purified racemic lasofoxifene" or "purified racemate"), and purified lasofoxifene D-tartrate, (−)cis-6(S)-phenyl-5(R)-[4-(2-pyrrolidin-1-ylethoxy)phenyl]-5,6,7,8-tetrahydronaphthalen-2-ol D-tartrate, which is useful as an estrogen agonist/antagonist, also known as a selective estrogen receptor modulator ("SERM"). Racemic lasofoxifene is an intermediate in the syntheses of lasofoxifene D-tartrate, having the following structure:

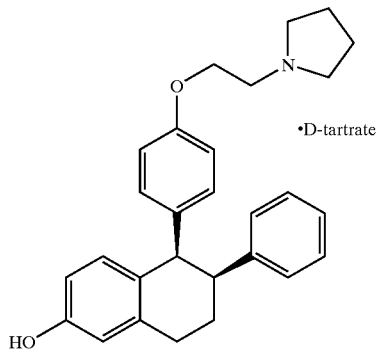

Lasofoxifene, lasofoxifene D-tartrate, its racemate and processes for the preparation thereof, are disclosed in commonly assigned U.S. Pat. No. 5,552,412, issued Sep. 3, 1996, and U.S. Pat. No. 5,948,809, issued Sep. 7, 1999. The text of these patents and all other references cited in this specification are hereby incorporated by reference in their entirety.

Typically, drug substances preferably contain less than 0.2%. impurities, most preferably less than 0.1% impurities. During the scale-up process for commercial production of lasofoxifene D-tartrate, however, it was determined that the resulting lasofoxifene D-tartrate compound contained undesirable impurities greater than 0.2%. It was also determined that purification of lasofoxifene D-tartrate to less than 0.1% impurities was not commercially feasible at the proposed scale-up. Consequently, there was a need to obtain an intermediate of Lasofoxifene D-tartrate, having a purity of less than 0.1% impurities. The process described within the instant invention resolves this issue.

SUMMARY OF THE INVENTION

This invention is directed to a method of purifying racemic, cis-6-phenyl-5-[4-(2-pyrrolidin-1-ylethoxy)phenyl]-5,6,7,8-tetrahydronaphthalen-2-ol, which comprises:

a) suspending racemic cis-6-phenyl-5-[4-(2-pyrrolidin-1-ylethoxy)phenyl]-5,6,7,8-tetrahydronaphthale-2-ol in a mixture of ethanol and tetrahydrofuran to form a suspension;

b) agitating and heating said suspension;

c) cooling said suspension of step (b); and d) collecting a solid purified racemic cis-6-phenyl-5-[4-(2-pyrrolidin-1-ylethoxy)phenyl]-5,6,7,8-tetrahydronaphthalen-2-ol.

In a preferred embodiment, said mixture of ethanol and tetrahydrofuran has about a 4:1 volume ratio In a preferred embodiment, said mixture of ethanol and tetrahydrofuran has about a 3.1 volume ratio.

In a more preferred embodiment, said mixture of ethanol and tetrahydrofuran has about a 2:1 volume ratio.

In a more preferred embodiment, said mixture of ethanol and tetrahydrofuran has about a 1:1 volume ratio.

In a preferred embodiment, said suspension formed in step (a) is agitated and heated from ambient temperature up to about 70° C. in step (b).

In a preferred embodiment, said suspension formed in step (a) is agitated and heated from ambient temperature up to about 65° C. for about 30 minutes to about 12 hours (b).

In a preferred embodiment, suspension so formed in step (b) is cooled and agitated for about 30 minutes to about 18 hours in step (c).

In a preferred embodiment, said suspension so formed in step (c) is collected by filtration, providing purified racemic cis-6-phenyl-5-[4-(2-pyrrolidin-1-ylethoxy)phenyl]-5,6,7,8-tetrahydronaphthalen-2-ol, having less than 0.1% impurities.

In another aspect, the invention is directed to purified racemic cis-6-phenyl-5-[4-(2-pyrrolidin-1-ylethoxy)phenyl]-5,6,7,8-tetrahydronaphthalen-2-ol.

The term "ambient temperature," as used here means about 15–25° C.

The terms "unpurified racemic lasofoxifene" or "racemate," as used herein, means the racemic mixture of cis isomers of cis-6-phenyl-5[4-(2-pyrrolidin-1-ylethoxy)phenyl]-5,6,7,8-tetrahydronaphthalen-2-ol prior to performing the purification process (i.e. greater than 0.1% impurities).

The terms "purified racemate lasofoxifene," or "purified racemate," as used herein, means racemic cis-6-phenyl-5[4-(2-pyrrolidin-1-ylethoxy)phenyl]-5,6,7,8-tetrahydronaphthalen-2-ol, having less that 0.1% impurities.

The term "purified lasofoxifene D-tartrate," as used herein, means (−)cis-6(S)-phenyl-5(R)-[4-(2-pyrrolidin-1- ylethoxy)phenyl]-5,6,7,8-tetrahydronaphthalen-2-ol D-tartrate, having less than 0.2% impurities.

DETAILED DESCRIPTION OF THE INVENTION

SCHEME I

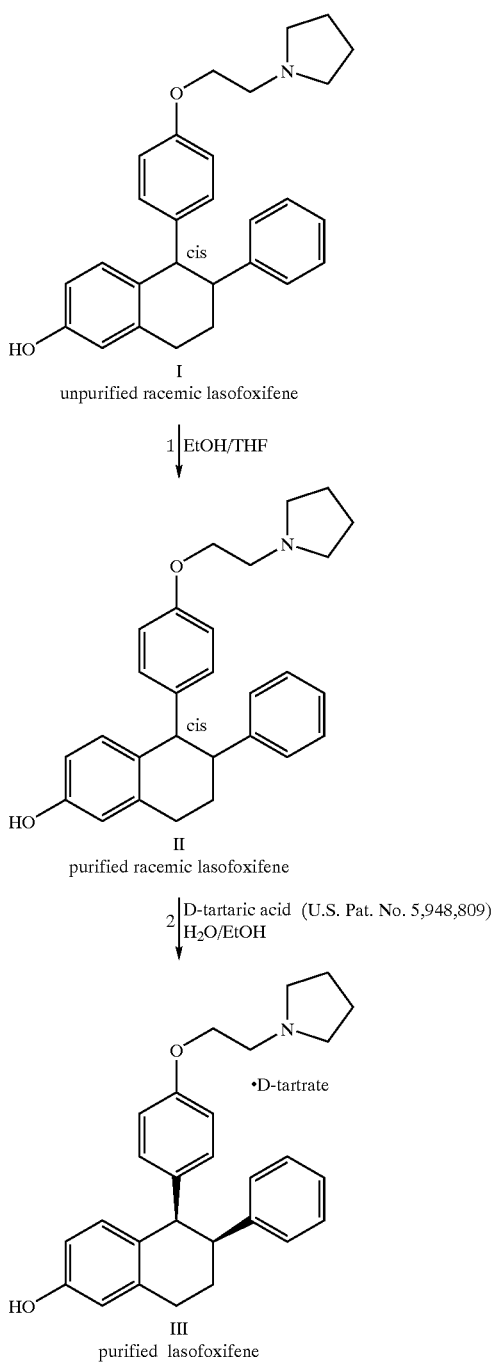

Lasofoxifene is a valuable estrogen/antagonist and is useful for, inter alia, oral contraception; relief for the symptoms of menopause; prevention of threatened or habitual abortion; relief of dysmenorrhea, relief of dysfunctional uterine bleeding; relief of endometriosis; an aid in ovarian development; treatment of acne; diminution of excessive growth of body hair in women (hirsuitism); the prevention and treatment of cardiovascular disease; prevention and treatment of arteriosclerosis; prevention and treatment of osteoporosis; treatment of benign prosatic hyperplasia and prostatic carcinoma obesity; and suppression of postpartum lactation. Lasofoxifene also has a beneficial effect on plasma lipid levels and, as such, is useful in treating and preventing hypercholesterolemia. While lasofoxifene is an estrogen agonist in bone, it is an antiestrogen in breast tissue and, as such would be useful in the treatment and prevention of breast cancer.

Racemic lasofoxifene is the cis-racemate of lasofoxifene, containing two asymmetric carbons corresponding to two optically active compounds. Resolution of the racemate has been accomplished by crystallization of the salt with R-(−)-1,1' binaphthyl-2,2'-diyl hydrogen phosphate ("R-binap"), as described in commonly owned U.S. Pat. No. 5,552,412. Resolution of the racemate was also accomplished by the addition of D-tartaric acid to the racemic or partially optically enriched cis-6-phenyl-5-[4-(2-pyrrolidin-1-ylethoxy)-5,6,7,8-tetrahydronaphthalene-2-ol, forming a 1:1 salt in aqueous ethanol, as described in U.S. Pat. No. 5,948,809. Upon cooling the (−) isomer is separated as a solid and is collected, providing the desired pharmaceutically acceptable salt of the (−) cis-D-tartrate isomer in high yield.

Several purification methods were explored to reduce the amount of impurities in lasofoxifene D-tartrate to less than 0.2%, including recrystallization and chromatography. These methods were unsatisfactory, either because of loss in yield or insufficient purity of lasofoxifene D-tartrate. It was determined that the desired level of purification (less than 0.1%) and optimal yield were obtained by the purification techniques described herein.

As set forth in Scheme I and the examples, unpurified racemic lasofoxifene is combined with a mixture of ethanol and tetrahydrofuran in Step 1(a). A person of ordinary skill in the art will appreciate that the ratio of ethanol to tetrahydrofuran may vary. Preferably, however, the volume ratio is 1:1 to 4:1.

In step 1(b), the resulting suspension was heated from about ambient temperature up to about 70° C. and agitated for a time period between about 30 minutes and up to about 12 hours. Preferably, however, the suspension is agitated for about 8 to about 12 hours. One of ordinary skill in the art will appreciate that the duration of agitation of the above suspension may be extended beyond 12 hours. In step 1(c), the heated suspension is then cooled to about ambient temperature with agitation for a time period from about 30 minutes to about 18 hours. Finally, in step 1(d), the solids may be collected by means known to those skilled in the art (e.g. filtration) and washed with an appropriate solvent (e.g. ethanol) and dried (e.g. in vacuo), providing purified racemic lasofoxifene.

The purified racemic lasofoxifene may be resolved, as depicted in Step II and described in U.S. Pat. No. 5,948,809, providing purified lasofoxifene D-tartrate.

A person of ordinary skill in the art would appreciate that the ratios of ethanol to tetrahydrofuran, the temperature, and the duration of heating and agitating may be varied. These variations are within the scope of this invention.

EXAMPLES

The examples below are intended to illustrate particular embodiments of the invention and are not intended to limit the specification, including the claims, in any manner.

Example 1

Purification of cis-6-phenyl-5-[4-(2-pyrrolidin-1-ylethoxy)phenyl]-5,6,7,8-tetrahydronaphthalen-2-ol with 2:1 Ethanol:Tetrahydrofuran 60 grams of unpurified racemic lasofoxifene was combined with 150 mL ethanol and 76.8 mL tetrahydrofuran. The resulting suspension was heated at about 65–70° C. and agitated for about 3 hours, cooled to ambient temperature and agitated for about an additional 18 hours. The solids were collected by filtration, washed twice with 25 mL ethanol, and dried in vacuo at about 45° C. to provide 49.36 grams of purified racemic lasofoxifene (82.3% yield).

The impurity profile of both the unpurified and purified racemic lasofoxifene were analyzed by reverse-phase High Pressure Liquid Chromatography (hereinafter "HPLC"), using a HPLC system with an ultraviolet ("UV") detector set at 230 nm and a Symmetry C18 cartridge column (50 mm length×3.9 mm I.D. at 40° C.). The mobile phase consisted of 1400:600:5:4 ratio v/v/v/v water:acetonitrile:trifluoroacetic acid:ammonium hydroxide, having a pH of 3.0 with a 2.0 mL/min flow rate. The retention time of racemic lasofoxifene is 5.7 minutes. The results are tabulated below and reported in percent (%) area.

TABLE 1

Percent impurities in unpurified and purified racemic lasofoxifene

| Relative Retention Times | 0.91 | 1.9 | 2.19 | 2.3 | 2.34 |
|---|---|---|---|---|---|
| Unpurified Racemic Lasofoxifene | 0.19 | 0.38 | 0.2 | 0.38 | 0.42 |
| Purified Racemic Lasofoxifene | <0.02 | 0.09 | <0.02 | <0.02 | <0.02 |

Example 2
Large Scale Purification of cis-6-phenyl-5-[4-(2-pyrrolidin-1-ylethoxy)phenyl]-5,6,7,8-tetrahydronaphthalen-2-ol with 2:1 Ethanol:Tetrahydrofuran 24.9 kilograms of unpurified racemic lasofoxifene was combined with 62 liters of ethanol and 31 liters of tetrahydrofuran. The resulting suspension was heated at about 60–65° C. and agitated for about 12 hours, cooled to ambient temperature and agitated for about an additional two hours. The solids were collected by filtration, washed with 22 liters of ethanol, and dried in vacuo at about 45° C. to provide 20.5 kg purified racemic lasofoxifene (82.3% yield).

The impurity profile of both unpurified and purified lasofoxifene was analyzed by HPLC, as described above. The results are tabulated below and reported in percent (%) area.

TABLE 2

Percent impurities in unpurified and purified racemic lasofoxifene

| Relative Retention Times | 0.91 | 1.9 | 2.19 | 2.3 | 2.34 |
|---|---|---|---|---|---|
| Unpurified Racemic Lasofoxifene | 0.19 | 0.38 | 0.2 | 0.38 | 0.42 |
| Purified Racemic Lasofoxifene | <0.02 | 0.05 | <0.02 | <0.02 | <0.02 |

Example 3
Purification of cis-6-phenyl-5-[4-(2-pyrrolidin-1-ylethoxy)phenyl]-5,6,7,8-tetrahydronaphthalen-2-ol with 2:1 Ethanol:Tetrahydrofuran 8.14 grams of unpurified racemic lasofoxifene was combined with 20 mL of ethanol and 10 mL of tetrahydrofuran. The resulting suspension was heated at about 60–65° C. and agitated for about 8 hours, cooled to ambient temperature and agitated for about two additional hours. The solids were collected by filtration, washed with 2 mL of ethanol, and dried in vacuo at about 40° C. to provide 6.81 grams of purified racemic lasofoxifene (83.7% yield).

The impurity profile of both unpurified and purified racemic lasofoxifene was analyzed by HPLC, as described above. The results are tabulated below and reported in percent (%) area.

TABLE 3

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.54 | 0.49 | 0.2 | 0.07 | 0.12 | 0.25 |
| Purified Racemic Lasofoxifene | <0.02 | 0.03 | 0.05 | 0.01 | <0.02 | <0.02 |

Example 4
Purification of cis-6-phenyl-5-[4-(2-pyrrolidin-1-ylethoxy)phenyl]-5,6,7,8-tetrahydronaphthalen-2-ol with 2:1 Ethanol:Tetrahydrofuran 8.2 grams of unpurified racemic lasofoxifene was combined with 41.1 mL of ethanol and 20.6 mL of tetrahydrofuran. The resulting suspension was heated at about 60–65° C. and agitated for about 8 hours, cooled to ambient temperature and agitated for about an additional two hours. The solids were collected by filtration, washed with 2 mL of ethanol and dried in vacuo at about 40° C. to provide 6.76 grams purified racemic lasofoxifene (82.5% yield).

The impurity profile of both unpurified and purified racemic lasofoxifene was analyzed by HPLC, as described above. The results are tabulated below and reported in percent (%) area.

TABLE 4

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.18 | 0.29 | 0.38 | <0.02 | 0.03 | 0.19 |
| Purified Racemic Lasofoxifene | <0.02 | 0.05 | 0.1 | <0.02 | <0.02 | <0.02 |

Example 5
Purification of cis-6-phenyl-5-[4-(2-pyrrolidin-1-ylethoxy)phenyl]-5,6,7,8-tetrahydronaphthalen-2-ol with 2:1 Ethanol:Tetrahydrofuran 8.2 grams of unpurified racemic lasofoxifene was combined with 13.7 mL of ethanol and 6.8 mL of tetrahydrofuran. The resulting suspension was heated at about 60–65° C. and agitated for about 8 hours, cooled to ambient temperature and agitated for about an additional two hours. The solids were collected by filtration, washed with 2 mL of ethanol, and dried in vacuo at about 40° C. to provide 7.65 grams of purified racemic lasofoxifene (93.3% yield).

The impurity profile of both unpurified and purified racemic lasofoxifene was analyzed by HPLC, as described above. The results are tabulated below and reported in percent (%) area.

TABLE 5

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.18 | 0.29 | 0.38 | <0.02 | 0.03 | 0.19 |
| Purified Racemic Lasofoxifene | <0.03 | 0.07 | 0.16 | <0.02 | <0.02 | 0.02 |

Example 6
Purification of cis-6-phenyl-5-[4-(2-pyrrolidin-1-ylethoxy)phenyl]-5,6,7,8-tetrahydronaphthalen-2-ol with 1:1 Ethanol:Tetrahydrofuran 4.0 grams of unpurified racemic lasofoxifene was combined with 7.5 mL of ethanol and 7.5 mL of tetrahydrofuran. The resulting suspension was heated at about 60–65° C. and agitated for about 8 hours, cooled to ambient temperature and agitated for about an additional two hours. The solids were collected by filtration, washed with 0.5 mL of ethanol, and dried in vacuo at about 40° C. to provide 3.31 grams of purified racemic lasofoxifene (82.8% yield).

The impurity profile of both unpurified and purified racemic lasofoxifene was analyzed by HPLC, as described above. The results are tabulated below and reported in percent (%) area.

TABLE 6

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.11 | 0.24 | 0.22 | <0.02 | 0.05 | 0.12 |
| Purified Racemic Lasofoxifene | >0.02 | 0.04 | 0.07 | <0.02 | <0.02 | <0.02 |

Example 7
Purification of cis-6-phenyl-5-[4-(2-pyrrolidin-1-ylethoxy)phenyl]-5,6,7,8-tetrahydronaphthalen-2-ol with 5:1 Ethanol:Tetrahydrofuran 4.0 grams of unpurified racemic lasofoxifene was combined with 12.5 mL of ethanol and 2.5 mL of tetrahydrofuran. The resulting suspension was heated at about 60–65° C. and agitated for about 8 hours, cooled to ambient temperature and agitated for about an additional two hours. The solids were collected by filtration, washed with 0.5 mL of ethanol and dried in vacuo at about 40° C. to provide 3.69 grams of purified racemic lasofoxifene (92.3% yield).

The impurity profile of both unpurified and purified racemic lasofoxifene was analyzed by HPLC, as described above. the results are tabulated below and reported in percent (%) area.

TABLE 7

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.11 | 0.24 | 0.22 | <0.02 | 0.05 | 0.12 |
| Purified Racemic Lasofoxifene | >0.02 | 0.08 | 0.13 | <0.02 | <0.02 | <0.02 |

Example 8
Attempted Purification of cis-6-phenyl-5-[4-(2-pyrrolidin-1-ylethoxy)phenyl]-5,6,7,8-tetrahydronaphthalen-2-ol with Ethanol 4.0 grams of unpurified racemic lasofoxifene was combined with 15 mL of ethanol. The resulting suspension was heated at about 60–65° C. and agitated for about 8 hours, cooled to ambient temperature and agitated for an additional two hours. The solids were collected by filtration, washed with 0.5 mL of ethanol, and dried in vacuo at about 40° C. to provide 3.31 grams of purified racemic lasofoxifene (82.8% yield).

The impurity profile of both unpurified and purified racemic lasofoxifene was analyzed by HPLC, as described above. The results are tabulated below and reported in percent (%) area.

TABLE 8

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.11 | 0.24 | 0.22 | <0.02 | 0.05 | 0.12 |
| Purified Racemic Lasofoxifene | 0.05 | 0.13 | 0.18 | <0.02 | <0.02 | 0.03 |

Example 9
Recrystallization of cis-6-phenyl-5-[4-(2-pyrrolidin-1-ylethoxy)phenyl]-5,6,7,8-tetrahydronaphthalen-2-ol with Tetrahydrofuran 4.0 grams of unpurified racemic lasofoxifene was combined with 15 mL of tetrahydrofuran. The resulting solution was heated at about 60–65° C. and agitated for about 8 hours, cooled to ambient temperature upon which no crystallization occurred. Crystallization commenced after seeding. The suspension was agitated at ambient temperature for about two hours. The solids were collected by filtration, washed with 0.5 mL of ethanol, and dried in vacuo at about 40° C. to provide 2.65 g product (66.3% yield).

The impurity profile of both unpurified and purified racemic lasofoxifene was determined by HPLC, as described above. The results are tabulated below and reported in percent (%) area.

TABLE 9

Percent impurities in unpurified and purified racemic lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 0.11 | 0.24 | 0.22 | <0.02 | 0.05 | 0.12 |
| Purified Racemic Lasofoxifene | <0.02 | <0.02 | 0.05 | <0.02 | <0.02 | <0.02 |

Example 10
Attempted Purification of lasofoxifene D-tartarte, (−)cis-6 (S)-phenyl-5(R)-[4-(2-pyrrolidin-1-ylethoxy)phenyl]5,6,7,8-tetrahydronaphthalen-2-ol D-tartrate by Recrystallization from Ethanol/Water 8.28 grams of unpurified lasofoxifene D-tartrate was dissolved in 166 mL of a 1:1 mixture of ethanol and water by heating at about 50° C. After filtration, the solution was slowly cooled to about 0° C., upon which crystallization commenced. The mixture was stirred at ambient temperature for about 48 hours. The solid was collected by filtration and washed twice with 10 mL ethanol. It was then dried in vacuo at about 45° C. to provide 6.37 grams of purified lasofoxifene D-tartrate (76.9% yield).

The impurity profile of both unpurified and purified lasofoxifene D-tartrate was analyzed by HPLC, as described above. The results are tabulated below and reported in percent (%) area.

TABLE 10

Percent impurities in unpurified and purified lasofoxifene D-tartrate

| Relative Retention Times | 0.92 | 2.06 | 2.14 | 2.26 | 2.38 |
|---|---|---|---|---|---|
| Unpurified Lasofoxifene | 0.21 | 0.16 | 0.07 | 0.28 | 0.11 |
| Purified Lasofoxifene | <0.02 | 0.14 | 0.04 | 0.32 | 0.09 |

Example 11
Large Scale Purification of Unpurified Racemic Lasofoxifene, cis-6-phenyl-5-[4-(2-pyrrolidin-1-ylethoxy)

phenyl]-5,6,7,8-tetrahydronaphthalen-2-ol with Ethanol/Tetrahydrofuran 20.4 kilograms of unpurified racemic lasofoxifene was combined with 50 liters of ethanol and 25 liters of tetrahydrofuran. The resulting suspension was heated at about 55–65° C. and agitated for about 8 hours, cooled to ambient temperature and agitated for about an additional four hours. The solids were collected by filtration, washed twice with 40 liters of ethanol, and dried in vacuo at about 40° C., providing 16.8 kilograms of purified racemic lasofoxifene (82.3% yield).

The impurity profile of both unpurified and purified racemic lasofoxifene was analyzed by HPLC, as described above. Results are tabulated below and reported in percent (%) area.

TABLE 11

Percent impurities in unpurified and purified lasofoxifene

| Relative Retention Times | 0.92 | 1.93 | 2.08 | 2.25 | 2.36 | 2.43 |
|---|---|---|---|---|---|---|
| Unpurified Racemic Lasofoxifene | 1.60 | 0.22 | <0.02 | <0.02 | 0.06 | 0.11 |
| Purified Racemic Lasofoxifene | 0.07 | <0.02 | <0.02 | <0.02 | <0.02 | <0.02 |

What is claimed is:

1. A method of purifying racemic cis-6-phenyl-5-[4-(2-pyrrolidin-1-ylethoxy)phenyl]-5,6,7,8-tetrahydronaphthalen-2-ol comprising:
   (a) suspending racemic cis-6-phenyl-5-[4-(2-pyrrolidin-1-ylethoxy)phenyl]-5,6,7,8-tetrahydronaphthalen-2-ol in a mixture of ethanol and tetrahydrofuran to form a suspension;
   (b) agitating and heating said suspension;
   (c) cooling said suspension of step (b); and
   (d) collecting a solid purified racemic cis-6-phenyl-5-[4-(2-pyrrolidin-1-ylethoxy)phenyl]-5,6,7,8-tetrahydronaphthalen-2-ol.

2. A method according to claim 1, wherein said mixture of ethanol and tetrahydrofuran has a 4:1 volume ratio.

3. A method according to claim 1, wherein said mixture of ethanol and tetrahydrofuran has a 3:1 volume ratio.

4. A method according to claim 1, wherein said mixture of ethanol and tetrahydrofuran has a 2:1 volume ratio.

5. A method according to claim 1, wherein said mixture of ethanol and tetrahydrofuran has a 1:1 volume ratio.

6. A method according to claim 1, 2, 3, 4 or 5, wherein said suspension formed in step (a) is agitated and heated from ambient temperature up to 70° C. in step (b).

7. A method according to claim 6, wherein said suspension formed in step (a) is agitated and heated from ambient temperature up to 65° C. for up to 12 hours in step (b).

8. A method according to claim 7 wherein said suspension so formed in step (b) is cooled and agitated up to 18 hours in step (c).

9. A method according to claim 8, wherein a solid, purified racemic cis-6-phenyl-5-[4-(2-pyrrolidin-1-ylethoxy)phenyl]-5,6,7,8-tetrahydronaphthalen-2-ol, in said suspension so formed in step (c) is collected by filtration, having less than 0.2% impurities.

10. A method according to claim 8, wherein a solid, purified racemic cis-6-phenyl-5-[4-(2-pyrrolidin-1-ylethoxy)phenyl]-5,6,7,8-tetrahydronaphthalen-2-ol, in said third suspension formed in step (c) is collected by filtration, having less than 0.1% impurities.

11. A method of purifying racemic cis-6-phenyl-5-[4-(2-pyrrolidin-1-ylethoxy)phenyl]-5,6,7,8-tetrahydronaphthalen-2-ol comprising:
   (a) suspending racemic cis-6-phenyl-5-[4-(2-pyrrolidin-1-ylethoxy)phenyl]-5,6,7,8-tetrahydronaphthalen-2-ol in a mixture of ethanol and tetrahydrofuran in a 2:1 volume ratio to form a suspension;
   (b) agitating and heating said suspension from ambient temperature up to 65° C. for up to 12 hours;
   (c) cooling said suspension so formed with agitation for up to 18 hours; and
   (d) collecting a solid racemic cis-6-phenyl-5-[4-(2-pyrrolidin-1-ylethoxy)phenyl]-5,6,7,8-tetrahydronaphthalen-2-ol by filtration.

* * * * *